US012228565B2

(12) United States Patent
Erdosy et al.

(10) Patent No.: US 12,228,565 B2
(45) Date of Patent: Feb. 18, 2025

(54) BLOOD CELL LYSIS COMPOSITIONS AND USES THEREOF

(71) Applicant: Instrumentation Laboratory Company, Bedford, MA (US)

(72) Inventors: Miklos Erdosy, Groton, MA (US); Hyoungsik Yim, Melrose, MA (US); Emily McDowell, Indianapolis, IN (US); Prasad V. A. Pamidi, Burlington, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

(21) Appl. No.: 17/348,934

(22) Filed: Jun. 16, 2021

(65) Prior Publication Data
US 2022/0412951 A1 Dec. 29, 2022

(51) Int. Cl.
*G01N 33/49* (2006.01)
*G01N 1/40* (2006.01)
*G01N 33/72* (2006.01)

(52) U.S. Cl.
CPC .......... *G01N 33/491* (2013.01); *G01N 1/4044* (2013.01); *G01N 33/721* (2013.01); *G01N 33/728* (2013.01)

(58) Field of Classification Search
CPC ...... G01N 33/49; G01N 33/491; G01N 33/72; G01N 33/721; G01N 33/728; G01N 1/4044; Y10T 436/10; Y10T 436/107497; Y10T 436/108331
USPC ........... 436/10, 17, 18, 63, 66, 97, 131, 175; 252/408.1
See application file for complete search history.

(56) References Cited

U.S. PATENT DOCUMENTS

| | | | | |
|---|---|---|---|---|
| 4,389,490 A * | 6/1983 | Crews | ...... | A01N 1/02 436/17 |
| 4,610,961 A * | 9/1986 | Guardino | ...... | C12Q 1/04 435/805 |
| 4,978,688 A | 12/1990 | Louderback | | |
| 6,573,102 B2 * | 6/2003 | Li | ...... | G01N 33/5002 436/63 |
| 7,851,207 B1 * | 12/2010 | Sagripanti | ...... | B01L 3/502 435/303.1 |
| 7,943,385 B2 * | 5/2011 | Yuan | ...... | G01N 33/723 436/66 |
| 9,850,521 B2 * | 12/2017 | Braman | ...... | C12Q 1/44 |
| 2003/0105197 A1 | 6/2003 | Collins et al. | | |
| 2004/0009496 A1 * | 1/2004 | Eiblmaier | ...... | C07H 21/04 536/25.4 |
| 2005/0145490 A1 * | 7/2005 | Shinno | ...... | G01N 33/66 204/403.01 |
| 2010/0240073 A1 * | 9/2010 | Wei | ...... | G01N 33/9493 435/7.25 |
| 2010/0291611 A1 * | 11/2010 | Bolbot | ...... | G01N 33/683 422/68.1 |
| 2011/0054157 A1 * | 3/2011 | Bitner | ...... | C12N 15/1017 536/25.4 |
| 2013/0171615 A1 * | 7/2013 | Van Meerbergen | ...... | C12Q 1/6806 435/6.15 |
| 2020/0222894 A1 | 7/2020 | Bosy et al. | | |
| 2021/0355454 A1 * | 11/2021 | Cardinal | ...... | A61K 35/76 |

FOREIGN PATENT DOCUMENTS

| | | |
|---|---|---|
| EP | 0184787 A2 | 6/1986 |
| EP | 0184787 A3 | 6/1986 |
| WO | 2004042003 A2 | 5/2004 |
| WO | 2004042003 A3 | 5/2004 |
| WO | 2014046990 A1 | 3/2014 |
| WO | 2015051117 A1 | 4/2015 |
| WO | 2022/081857 * | 4/2022 |

OTHER PUBLICATIONS

The Dow Chemical Company, "TERGITOL™ 15-S-9 Surfactant Product Information," Technical Data Sheet Form No. 119-01950-1107, May 2021, (2 pages).
The Dow Chemical Company, "Spectrophotometric Method for the Determination of Nonionic Surfactants," Form No. 119-02662-01, Jan. 1986, (1 page).
The Dow Chemical Company, "Tergitol® Material Safety Data Sheet," Form No. sc-253623, Apr. 12, 2009, (11 pages).
The Dow Chemical Company, "Components for antimicrobial formulations," Form No. 119-02631-01-1121 S2D, Jan. 2021, (6 pages).
The Dow Chemical Company, "Dow sustainable nonionic surfactants in institutional laundry cleaning," Form No. 119-02591-01-0221 S2D, Jan. 2021, (4 pages).
The Dow Chemical Company, "Dow Surfactants Reference Chart," Form No. 119-01491-01-0621 S2D, Jan. 2021, (16 pages).
QED Environmental Systems, Inc., "GEM5000 Gas Analyzer Operating Manual," Form No. OMGEM5KN4.7.1, Jan. 2021, (70 pages).
Extended European Search Report for European Patent Application No. 22176850.0, issued Oct. 19, 2022, (15 pages).
Elko, Evan A. et al,. "Oxidation of peroxiredoxin-4 induces oligomerization and promotes interaction with proteins governing protein folding and endoplasmic reticulum stress". J Biol Chem. Jan.-Jun. 2021;296:100665. doi: 10.1016/j.jbc.2021.100665. Epub Apr. 23, 2021. PMID: 33895140; PMCID: PMC8141880, (12 pages).
Chow, Sue et al., "Whole Blood Fixation and Permeabilization Protocol with Red Blood Cell Lysis for Flow Cytometry of Intracellular Phosphorylated Epitopes in Leukocyte Subpopulations". 2005 International Society for Analytical Cytology, Ontario, Canada, Aug. 20, 2004 (14 pages).

(Continued)

*Primary Examiner* — Maureen Wallenhorst
(74) *Attorney, Agent, or Firm* — ArentFox Schiff LLP (57) ABSTRACT

An example blood cell lysis composition includes a buffer and a secondary alcohol ethoxylate at a concentration in the range of about 2.5 percent (%) to about 20% weight per volume (w/v). The secondary alcohol ethoxylate may include Tergitol™ TMN-100X or Tergitol™ 15-S-9. The composition may be configured to lyse at least 90% of blood cells in a blood sample.

17 Claims, 8 Drawing Sheets

(56) References Cited

OTHER PUBLICATIONS

Kim Seunghyeon et al: "Developing a SARS-CoV‑2 Antigen Test Using Engineered Affinity Proteins", ACS applied materials & interfaces, Apr. 19, 2021 (Apr. 19, 2021), pp. 38990-39002, XP055840136, DOI: 10.1021 / acsami.1c08174, Retrieved from the Internet: URL:https://chemrxiv.org/engage/api-gateway/chemrxiv/assets/orp/resource/item/60c757a6469df4a17df454fb/original/developin-a-sars-co-v-2-antigen-test-using-engineered-affinity-proteins.pdf [retrieved on Sep. 13, 2021].

Pitel J.A. et al: "Methods to extract NAD'A-malate dehydrogellase efficiently from white spruce needles", Physiol. Plant. 65, Jan. 1, 1985 (Jan. 1, 1985), pp. 129-134, XP055969992, Retrieved from the Internet: URL:https://onlinelibrary.wiley.com/doI/epdf/10.1111/j.1399-3054.1985.tb02371.x [retrieved on Oct. 11, 2022].

Anonymous: "Technical Data Sheet of Tergitol(TM) NP-40 Product Information from Dow", Dec. 10, 2019 (Dec. 10, 2019), pp. 1-2, XP055969791, Retrieved from the Internet: URL:https://www.dow.com/content/dam/doc/docu ments/en-us/ productdatasheet/119/119-01929-01-tergitol-np-40-surfactant-tds.pdf [retrieved on Oct. 11, 2022].

Authorization List' of Annex XIV of REACH Regulation 1907/2006/EC (https://echa.europa.eu/authorisation-list accessed Jul. 28, 2023).

Product Data Sheet for "Ethonas NP-40 (70% aq)," Petronas Chemicals Group Berhad (PCGB) [online] Retrieved from the Internet URL:<https://www.petronas.com/pcg/sites/default/files/2023-07/Products_Documents_NP-40%20(70%20aq)_May23%20SCA.pdf> (© 2023), [retrieved on Dec. 11, 2023], 1 page.

Silva et al., "Isothiazolinone Biocides: Chemistry, Biological, and Toxicity Profiles," Molecules 25:991 (2020), 22 pages.

DuPont Microbial Control Technical Data Sheet for KATHON CG/ICP, CG/ICP II, and CG/ICP III Preservatives (© 2020), 8 pages.

\* cited by examiner

BLOOD CELL LYSIS COMPOSITIONS AND USES THEREOF

TECHNICAL FIELD

This specification relates generally to example blood cell lysis compositions and uses thereof.

BACKGROUND

During optical diagnostics, whole blood samples cause light scattering that may affect measurement accuracy. Lysing cells of the whole blood sample may reduce such light scattering.

SUMMARY

An example blood cell lysis composition includes a buffer and a secondary alcohol ethoxylate at a concentration in the range of about 2.5 percent (%) to about 20% weight per volume (w/v). The blood cell lysis composition may include one or more of the following features, either alone or in combination.

The secondary alcohol ethoxylate may include at least one of the following: Tergitol™ Type 15-S-12, Tergitol™ Type 15-S-30, Tergitol™ Type 15-S-5, Tergitol™ Type 15-S-7, Tergitol™ Type 15-S-9, Tergitol™ Type NP-10, Tergitol™ Type NP-4, an ethoxylated nonylphenol of Tergitol™ Type NP-40, a sodium (3,9-diethyltridecane-6-sulfonate) of Tergitol™ Type NP-7, a sodium (2-ethylhexyl sulfate) of Tergitol™ Type 8, Tergitol™ Type NP-9, Tergitol™ TMN-100X, a sodium (7-ethyl-2-methylundecan-4-yl) sulfate of TEOS Tergitol™, Tergitol™ TMN-10, or Tergitol™ TMN-6. The secondary alcohol ethoxylate may be Tergitol™ TMN-100X or Tergitol™ 15-S-9.

The buffer may include at least one of 3-(N-Morpholino)propanesulfonic acid (MOPS), phosphate buffer (PBS), 4-(2-hydroxyethyl)-1-piperazineethanesulfonic acid (HEPES), 2[[1,3-dihydroxy-2-(hydroxymethyl)propan-2-yl]amino]ethanesulfonic acid (TES), 2,2-Bis(hydroxymethyl)-2,2',2"-nitrilotriethanol, or 2-Bis(2-hydroxyethyl)amino-2-(hydroxymethyl)-1,3-propanediol (Bis-Tris).

The blood cell lysis composition may include a biocide. The biocide may include at least one of 5-chloro-2-methyl-4-isothiazolin-3-one (CMIT), 2-methyl-4-isothiazolin-3-one (MIT), Proclin 300, 1,2-Benzisothiazolin-3-one (BIT), dodecylguanidine hydrochloride (DGH), gentamycin, levofloxacin, colistin, octylisothiazolinone (OIT), or amikacin. The biocide may include CMIT and MIT. The CMIT and the MIT may be in a ratio of about 3:1 (CMIT:MIT). The CMIT:MIT may be at a concentration of 1% (w/v) in the blood cell lysis composition.

The blood cell lysis composition may have a pH between about 6 and about 8. The secondary alcohol ethoxylate may be present at a concentration in the range of about 5% to about 18% (w/v). The secondary alcohol ethoxylate may be present at a concentration in the range of about 9% to about 14% (w/v). The secondary alcohol ethoxylate may be biodegradable. The blood cell lysis composition may be configured to lyse at least 90% of blood cells in a sample in less than 2 seconds. The secondary alcohol ethoxylate may have a 5 minute (0.1 weight % active) foam height from about 75 millimeter (mm) to about 125 mm. The secondary alcohol ethoxylate may have a 5 minute (0.1 weight % actives) foam height from about 40 mm to about 75 mm.

An example method for determining a level of a hemoglobin in a blood sample includes (i) mixing the blood cell lysis composition with a blood sample, thereby lysing one or more cells in the blood sample, and (ii) determining the level of the hemoglobin in the blood sample. The example method may include one or more of the following features, either alone or in combination.

The hemoglobin may include least one of oxyhemoglobin, de-oxyhemoglobin, carboxyhemoglobin, methemoglobin, sulfhemoglobin, cyanmethemoglobin, or fetal hemoglobin. The method may include measuring a level of bilirubin.

An example method of making a blood lysing composition includes mixing a buffer with a secondary alcohol ethoxylate in a concentration in the range of about 2.5 percent (%) to about 20% weight per volume (w/v). The example method may include one or more of the following features, either alone or in combination.

The secondary alcohol ethoxylate may have a 5 minute (0.1 weight % active) foam height from about 40 mm to about 75 mm. The secondary alcohol ethoxylate may be or include Tergitol™ TMN-100X or Tergitol™ 15-S-9.

An example blood cell lysis composition includes (i) a buffer, and (ii) a secondary alcohol ethoxylate that is or that includes Tergitol™ TMN-100X or Tergitol™ 15-S-9. The blood cell lysis composition may include one or more of the following features, either alone or in combination.

The secondary alcohol ethoxylate may be at a concentration in the range of about 9% to about 14% (w/v). The composition may be configured to lyse at least 90% of cells in a sample in less than 2 seconds.

Two or more of the features described in this specification, including in this summary section, may be combined to form implementations not specifically described in this specification.

The details of one or more implementations are set forth in the accompanying drawings and the description below. Other features and advantages will be apparent from the description and drawings, and from the claims.

DETAILED DESCRIPTION

A CO-Oximeter is a device that measures concentrations of different hemoglobins and oxygen saturation of hemoglobin in a blood sample. Oxygen saturation or "$sO_2$" of a blood sample corresponds to the proportion of functional hemoglobins with bound oxygen in the blood sample.

An example CO-Oximeter includes an optical system configured to measure different forms of hemoglobin and oxygen saturation based on the optical absorbance of hemoglobin forms in a blood sample. For example, a CO-Oximeter may be configured to measure the optical absorbance of one or more of the following: functional hemoglobin species including oxygen-carrying oxyhemoglobin ($O_2$Hb) and de-oxyhemoglobin (HHb), or dysfunctional hemoglobin derivatives such as carboxyhemoglobin (COHb), methemoglobin (MetHb), sulfhemoglobin (SHb), and cyanmethhemoglobin (CNmetHb). An example CO-Oximeter of the type described herein may also be configured to simultaneously measure fetal hemoglobin, adult hemoglobin, and the concentration of bilirubin in a blood sample. Bilirubin is a hemoglobin degradation byproduct, as described below.

CO-Oximetry measurements may be used to diagnose various medical conditions including, but not limited to, anemia, suspected carbon monoxide poisoning, or other non-respiratory hypoxic disorders, blood disorders, circulatory problems, and lung diseases. CO-Oximetry measurements may depend on accurate measurements of light scattering in the optical system. In this regard, whole blood cell samples may scatter more light in an optical system than lysed blood cell samples. Therefore, it may be beneficial to lyse blood samples prior to obtaining CO-Oximetry spectral measurements using those samples. The lysed blood samples may reduce optical scattering, which may produce more accurate and precise CO-Oximetry measurements.

Accordingly, the example systems and processes described herein include mixing blood cell lysis compositions with whole blood samples prior to obtaining CO-Oximetry spectral measurements. The blood cell lysis compositions lyse the blood sample. Lysing includes breaking down the cell membranes of the whole blood cells thereby releasing the lysate, including hemoglobin, from the whole blood cells. Any one or more of the example blood cell lysis compositions described herein (referred to collectively as "the blood cell lysis composition") may be used to lyse whole blood samples in the context of CO-Oximetry or other processes.

As noted, a lysed blood sample may produce less light scattering than whole blood during CO-Oximetry, which may result in more accurate CO-oximetry measurements. Example blood cell lysis compositions include one or more surfactants, one or more buffer solutions ("buffers"), biocide, and DI (deionized) water. Surfactants include compounds that lyse cells by disrupting cellular membranes in order to release the lysate. A surfactant may be synthesized, for example, via the reaction of a fatty alcohol and ethylene oxide. An example surfactant that may be used in lysing a whole blood sample includes an alcohol ethoxylate. An example alcohol ethoxylate has a chemical formula of $R(OC_2H_4)_nOH$. Here, R refers to an attached hydrogen or hydrocarbon side chain, and n refers to the number of ethylene oxide ($OC_2H_4$) units.

An example blood cell lysis composition includes a nonionic surfactant, such as a secondary alcohol ethoxylate, in a buffer having a preservative therein, possibly with DI water and a biocide. The secondary alcohol ethoxylate functions to lyse the blood sample when the blood cell lysis composition is mixed with whole blood prior to performing CO-Oximetry. The secondary alcohol ethoxylate may include 11 to 15 ethylene oxide units, which may be commercialized under the trade name of Tergitol™. Example secondary alcohol ethoxylates under this trade name include, but are not limited to, Tergitol™ Type 15-S-12, Tergitol™ Type 15-S-30, Tergitol™ Type 15-S-5, Tergitol™ Type 15-S-7, Tergitol™ Type 15-S-9, Tergitol™ Type NP-10, Tergitol™ Type NP-4, an ethoxylated nonylphenol of Tergitol™ Type NP-40, a sodium sulfate (3,9-diethyltridecane-6-sulfonate) of Tergitol™ Type NP-7, a sodium sulfate (2-ethylhexyl sulfate) of Tergitol™ Type 8, Tergitol™ Type NP-9, Tergitol™ TMN-100X, a sodium sulfate (7-ethyl-2-methylundecan-4-yl) of TEOS Tergitol™, Tergitol™ TMN-10, or Tergitol™ TMN-6. Other examples of secondary alcohol ethoxylates that may be included in a blood cell lysis composition include, but are not limited to, ECOSURF™, e.g., ECOSURF™ EH-9 and ECOSURF™ SA-9.

Example secondary alcohol ethoxylate chemical structures that may represent nonionic surfactants that can be part of the example blood cell lysis composition include, but are not limited to, the following.

(1) Tergitol™ NP-10, where z=10, and where the chemical structure is as follows.

(2) Tergitol™ 15-S-7, where x=7 and Tergitol™ 15-S-9, where x=9, and where the chemical structure is as follows.

(3) Tergitol™ TMN-6, where n=6 and Tergitol™ TMN-10, where n=10, and where the chemical structure is as follows.

(4) Tergitol™ TMN-100X, which may include a 70:30 ratio of Tergitol™ TMN-10 to Tergitol™ TMN-6.

In some implementations, an example blood cell lysis composition that includes a surfactant described herein may include one or more of the secondary alcohol ethoxylates at one or more of the following concentrations: between about 2.0 percent (%) or 2.5% to about 20% weight per volume (w/v), between 5% to 18% (w/v), between 9% to 14% (w/v), between 9% to 11% (w/v), between 9 to 10% (w/v), between 9.0% to 9.5% (w/v), between 10% to 12% (w/v), between 10% to 11% (w/v), between 10.0% to 10.5% (w/v), between 11% to 13% (w/v), between 11% to 12% (w/v), between 11.0% to 11.5% (w/v), between 12% to 14% (w/v), between 12% to 13% (w/v), between 12.0% to 12.5% (w/v), between 13% to 14% (w/v), or between 13.0% to 13.5% (w/v).

Surfactants used for lysing, including the secondary alcohol ethoxylates described herein, may lower surface tension in a liquid blood sample and induce foam formation in the blood sample as air is mixed into the blood sample. Foam is detrimental to optical absorbance measurements because it causes additional light scattering. In some implementations, surfactants for performing cell lysis in CO-Oximetry may reduce or minimize foam formation and/or produce foam that dissipates quickly prior to spectral measurements. Example surfactants used for lysing may include a secondary alcohol ethoxylate that has a surface tension of between 20 to 40 dynes/cm (centimeter) inclusive when measured with 1% actives at 25° C. (Celsius). Example surfactants used for lysing may include a secondary alcohol ethoxylate that has a measured foam height of less than 110 mm (millimeter) in water based solutions at 0.1 weight % actives. Standard measurements of the foam height may be taken, for example, five minutes after addition of the surfactant to a water based solution. The foam height produced by a secondary alcohol ethoxylate may be measured, for example, using the Ross-Miles method. In an example implementation, the surfactant has a 5 minute (0.1 weight % active) foam height from about 75 millimeter (mm) to about 125 mm. In an example implementation, the surfactant has a 5 minute (0.1 weight % active) foam height from about 40 mm to about 75 mm.

In the context of CO-Oximetry, turbidity is a measure of the amount of light scattering experienced by the optical system when light shines through a blood sample. Optical clarity may be a function of turbidity of the blood sample, for example, the less light scattered by the blood sample, the greater will be the optical clarity associated with the blood sample. In some implementations, the example blood cell lysis compositions described herein lyse 90% to 100% of cells in a whole blood sample within 1 to 3 seconds in order to reduce the effects of scattering and improve target optical clarity during CO-Oximetry. In this regard surfactants containing secondary alcohol ethoxylates having similar structures to those of Tergitol™ 15-S-9 and/or Tergitol™ TMN-100X may be used to lyse at least 90% of blood cells within 1 to 3 seconds.

In some implementations, nonionic surfactants other than those described previously may be used to perform blood cell lysis in a CO-Oximetry context or elsewhere. For example, octylphenol ethoxylates may be part of a blood cell lysis composition used to lyse a blood sample, such as a whole blood sample. Example octylphenol ethoxylates include an ethylene oxide adduct of octylphenol. Triton X-100 is an example octylphenol ethoxylate that may be used to lyse blood samples. Triton X-100 has the following chemical structure.

In some implementations, example blood cell lysis compositions may include a buffer in addition to a surfactant. An example buffer includes an aqueous solution that resists changes in pH by neutralizing small amounts of added acid or base using a weak acid and its salt or a weak base and its salt. Examples of buffers that may be used in the blood cell lysis compositions described herein include, but are not limited to, the following: 3-(N-Morpholino) propane sulfonic acid (MOPS), phosphate buffer (PBS), 4-(2-hydroxyethyl)-1-piperazineethanesulfonic acid (HEPES), 2[[1,3-dihydroxy-2-(hydroxymethyl)propan-2-yl]amino] ethanesulfonic acid (TES), 2,2-Bis(hydroxymethyl)-2,2',2"-nitrilotriethanol, or 2-Bis(2-hydroxyethyl)amino-2-(hydroxymethyl)-1,3-propanediol (Bis-Tris). In some implementations, the buffer may include 3-(N-Morpholino) propane sulfonic acid (MOPS). In some implementations, the buffer maintains the pH of the blood cell lysis composition between 6 and 8. In some implementations, the buffer is selected to reduce the impact of spectral changes of hemoglobin from pH on CO-Oximetry measurements, for example, the change in pH can alter absorbance spectrum and measurements of MetHb or other substances.

In some implementations, the example blood cell lysis compositions described herein may include a biocide. An example biocide includes compounds that are intended to destroy, deter, render harmless, or exert a controlling effect on any harmful organism that may be present in the blood cell lysis composition. Examples of biocides that may be used in the blood cell lysis composition include, but are not limited to, the following: 5-chloro-2-methyl-4-isothiazolin-3-one (CMIT), 2-methyl-4-isothiazolin-3-one (MIT), CMIT:MIT in a ratio of about 3:1 under the trade name Proclin™ 300, 1,2-Benzisothiazolin-3-one (BIT), dodecylguanidine hydrochloride (DGH), gentamycin, levofloxacin, colistin, octylisothiazolinone (OIT), or amikacin. In some implementations, the CMIT:MIT biocide may be at a concentration of 1% weight per volume (w/v) in the blood cell lysis composition.

A CO-Oximeter may be part of a system that performs measurements at a point-of-care (POC) site or central laboratory. Anemia, blood disorders, circulatory problems, and lung diseases affect blood oxygen saturation levels and, if left untreated, can cause organ damage or death. CO-Oximeters may be used at POC sites and/or central laboratories to determine oxygen saturation of hemoglobin, total hemoglobin or functional or dysfunctional hemoglobins in a blood sample, which may be evidence of such disorders. The blood cell lysis compositions described herein may be used to improve CO-Oximetry measurements by reducing scattering effects from red blood cells and by buffering the lysed blood samples to reduce or to minimize pH impact on spectral measurements performed by the CO-Oximeter. In this regard, in some implementations, the CO-Oximeter system may also measure pH, $pO_2$, $pCO_2$, $Na^+$, $K^+$, $Ca^{2+}$, $Cl^-$, glucose, lactate, and/or hematocrit of a blood sample, in addition to performing CO-Oximetry and/or bilirubin measurements.

Figure 1A:
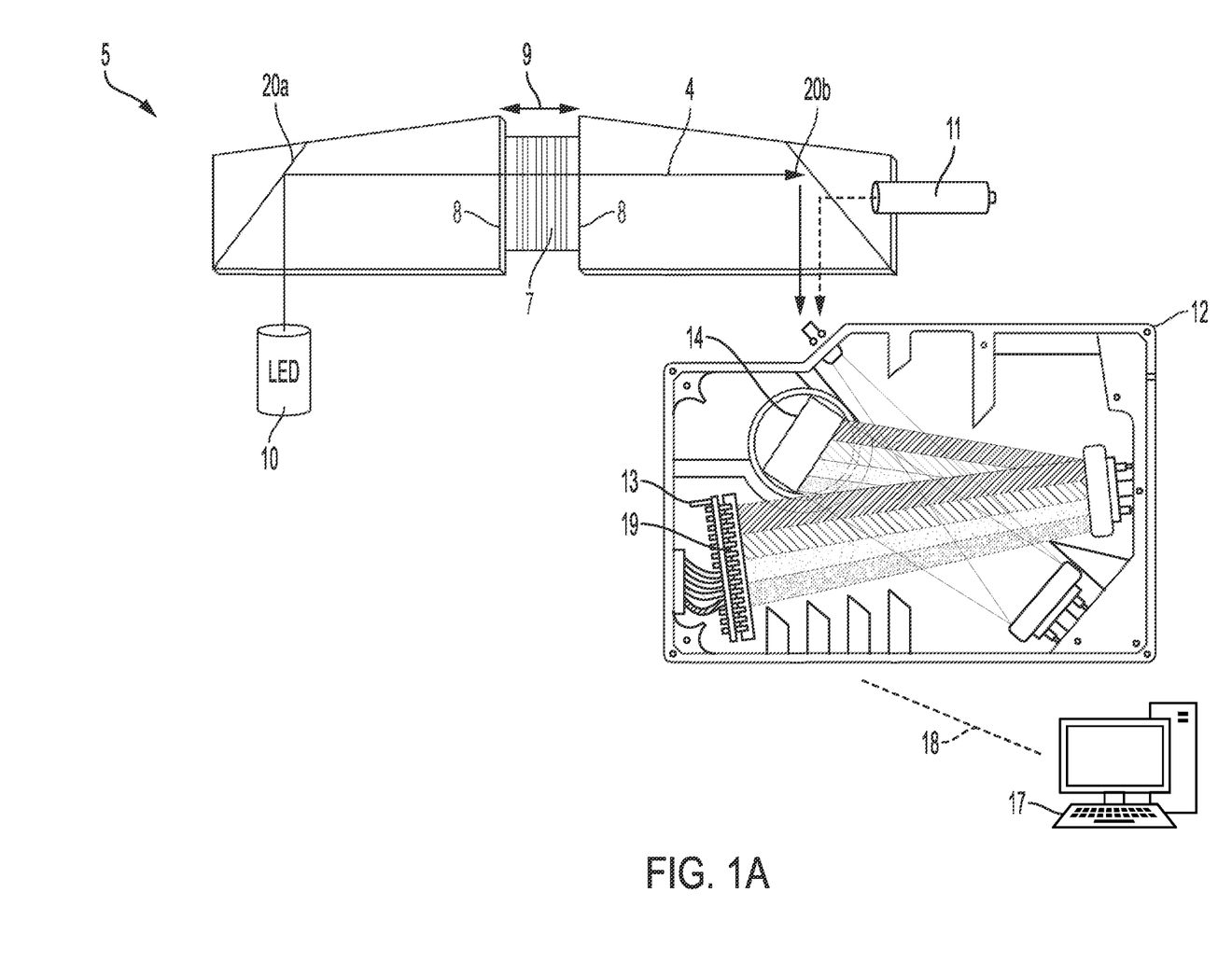
FIG. 1A is a block diagram showing an example optical system for performing CO-Oximetry measuring on a blood sample.

FIG. 1A shows an example CO-Oximeter system 5. CO-Oximeter system 5 includes an optical absorbance system configured to illuminate a blood sample and to determine a spectral absorbance of the blood sample. The blood sample analyzed by CO-Oximeter system 5 may be a whole blood sample that is lysed using one or more of the blood cell lysing compositions described herein. More specifically, in example CO-Oximeter 5, a blood cell lysis composition and a blood sample are introduced into a mixing chamber—e.g., through a mixing valve—in an optical cell 7. Movement of the blood sample and blood cell lysis composition through the mixing chamber under simultaneous actuation implemented by a solenoid causes the blood sample and lysis composition to simultaneously mix and lyse the red blood cells. The resulting mixture constitutes a lysed blood sample that is usable to obtain optical absorbance measurements by the CO-Oximeter with a reduction or elimination of scattering effects caused by red blood cells.

CO-Oximeter 5 also includes a broad-spectrum white light-emitting diode (LED) light source 10 to illuminate lysed blood in the mixing/optical chambers and a neon light 11, having a high signal-to-noise ratio, which may be used as a wavelength reference for optical absorbance measurements. Example CO-Oximeter 5 also includes a high-resolution spectrometer 12 having a holographic diffraction grating 14 and a charge-coupled device (CCD) 19 contained in compartment 13. CCD 19 includes an integrated circuit, which may include an array of capacitors to provide high signal-to-noise digital imaging. CCD 19 is in communication with a computing system 17. This communication may be wired or wireless and is represented by dotted line 18. Computing system 17 is configured to perform computational analyses to resolve sample spectra detected by the CO-Oximeter, as described below.

In CO-Oximeter 5, the lysed blood sample is illuminated in optical cell 7 by light 4 emitted from source 10. Light 4 reflects from mirrors 20a, 20b through optical cell 7 containing the lysed blood sample to spectrometer 12. In some implementations, optical cell 7 includes two parallel plate optical windows 8 separated by a path length 9 through which light 4 passes towards spectrometer 12. The wavelength constituents of the light that passes through the lysed blood sample are separated, in spectrometer 12, by holographic diffraction grating 14. The constituents are directed to, and impact, CCD 19. CCD 19 generates charge based on the incident light, which is read by electronics and turned into a digital copy of the light patterns falling on CCD 19.

Light source 10 may be controllable—for example, by computing system 17—to illuminate the lysed blood sample over a range of wavelengths, such as 480 nm (nanometers) to 650 nm. Spectrometer 12 may measure light through the lysed blood sample at the different wavelengths. Performing measurements at different, or over a range of different, wavelengths enables CO-Oximeter 5 to distinguish between absorbance spectra of different hemoglobin types or derivatives. In an example, absorbance of a component of the blood sample, for example a hemoglobin derivative, includes the attenuation of transmitted radiant power through the component caused by the physical process of absorption taking into account reflection, scattering, or other physical phenomena. From the measured spectral values, a noise-corrected absorbance of the hemoglobin or hemoglobin derivative in the blood sample may be determined using the following equation:

$$\text{Abs} = \log_{10}[\text{IB}/\text{IS}].$$

In the preceding equation, IB refers to dark-corrected intensity spectra for a process control solution (PCS) B. The PCS-B is a colorless solution used to provide a zero-concentration reference for the CO-Oximetry process. In the preceding equation, IS refers to dark-corrected intensity spectra of the hemoglobin or hemoglobin derivative.

Data regarding the absorption of different hemoglobin or hemoglobin derivatives in the blood sample is sent from spectrometer 12 to computing system 18, where that data may be analyzed, processed, and presented in a graphical user interface (GUI) to a user. For example, absorbance spectra of hemoglobin and/or hemoglobin-related products may be collected and stored in computer memory. Computing system 17 may use this data to determine the concentration of hemoglobin and/or hemoglobin-related products in a blood sample. Based on this information, measurements such as total hemoglobin (tHb), which may refer to the total concentration of hemoglobin in a blood sample, may be obtained.

Figure 1B:
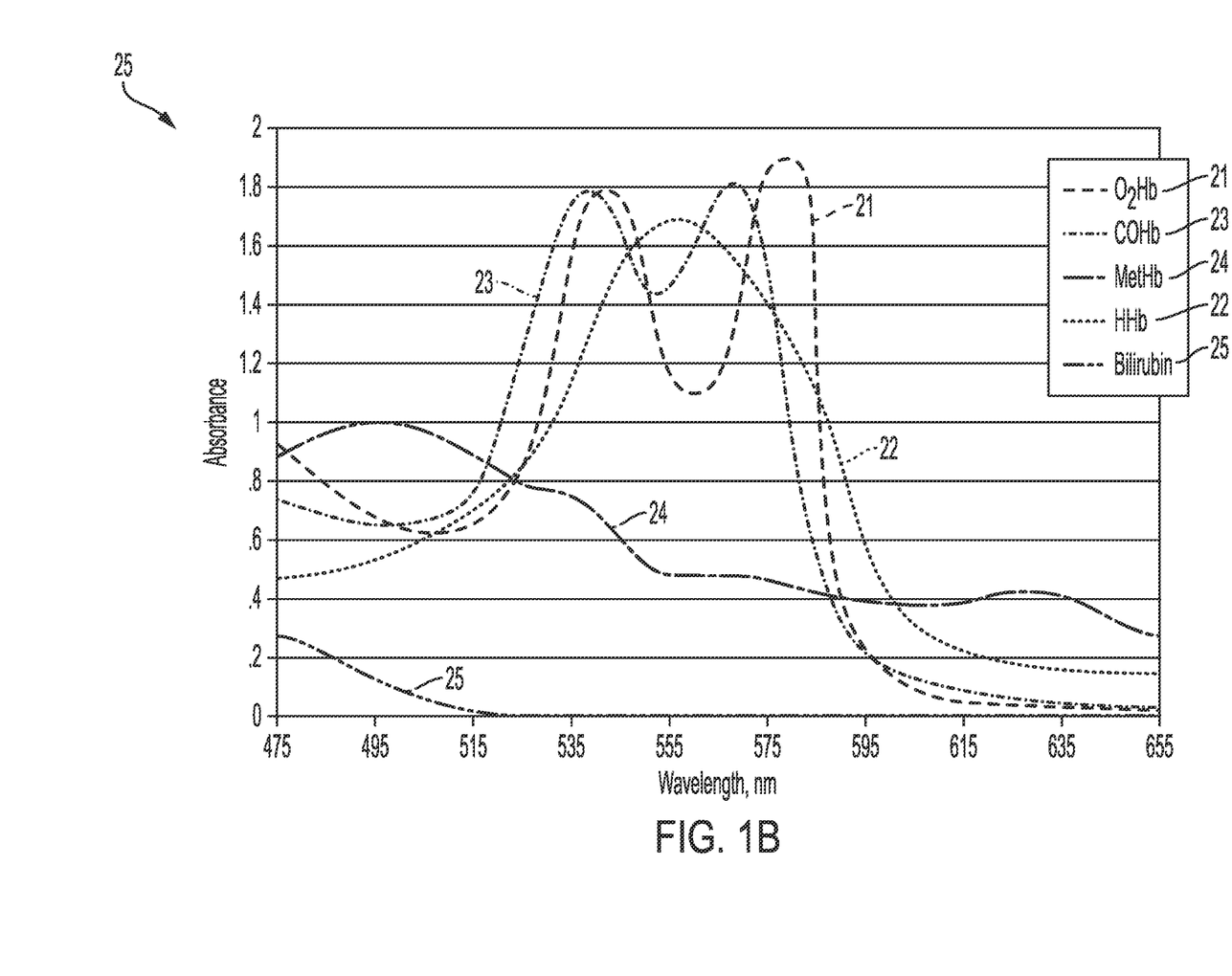
FIG. 1B is a graph showing absorbance measurements obtained using the example optical system.

Referring to FIG. 1B, computing system 17 may also generate a GUI 25. GUI 25 plots optical absorbance (y-axis) for various different wavelengths of light (x-axis) for different hemoglobin and/or hemoglobin-related products in a lysed blood sample. In GUI 25, the different hemoglobins and/or hemoglobin-related products include $O_2Hb$ 21, HHb 22, COHb 23, MetHb 24, and bilirubin 25.

As noted previously, oxygen saturation or "$sO_2$" corresponds to the fraction of oxygen-saturated hemoglobin relative to total functional hemoglobin in a blood sample. $sO_2$ may be predictive of the amount of oxygen available for tissue perfusion. In some implementations, $O_2Hb$ and HHb concentrations that are based on CO-Oximetry measurements may be used by the computing system to determine oxygen saturation of hemoglobin in a blood sample. An equation to determine oxygen saturation in the blood sample is the following:

$$sO_2 = 100 \times [O_2Hb/(O_2Hb + HHb)]\%.$$

CO-Oximeter 5 and computing system 17 may be configured to determine the amount of bilirubin in a lysed blood sample. In this regard, bilirubin is a yellow compound that occurs in the normal catabolic pathway break-down of hemeprotein ("heme") in vertebrates. This catabolism may be a necessary process in the body's clearance of waste products that arises from the destruction of aged or abnormal red blood cells. To measure bilirubin, its light absorbance as determined by CO-Oximeter 5 may be compared to pre-defined standards based on Beer Lambert's Law. In this regard, the following equation may be used by the computing system to determine light absorbance of bilirubin in a blood sample.

$$A = \log_{10}(\text{IB}/\text{IS}) = \varepsilon CL$$

Above, A is a value corresponding the absorbance of light by the lysed blood sample, IB and IS are as described above, C is a concentration of the solution containing the lysed blood sample, $\varepsilon$ is the molar extinction coefficient, and L is the path length over which the light travels. Total bilirubin may be reported as a plasma equivalent concentration. In this regard, when whole blood is analyzed, hematocrit correction may be performed by the computing system to adjust for the dilution effect from red blood cells and thereby obtain the plasma equivalent concentration. The hematocrit correction may be performed using the following equation.

$$\text{Bili}_p = \text{Bili}_b/(1 - \text{Hct})$$

Above, $\text{Bili}_p$ corresponds to the concentration of total bilirubin in the plasma phase, $\text{Bili}_b$ corresponds to the concentration of total bilirubin in whole blood, and Hct represents the hematocrit expressed as a fraction. Hct is determined by multiplying total hemoglobin grams per deciliter (g/dL) by a constant of 0.03. The constant 0.03 is based on an example average concentration of hemoglobin in red blood cells.

The blood cell lysis composition described herein can be used for optical clinical chemistry or immunoassays not specifically described herein and with instruments other than that shown in FIG. 1A. Described below are experiments performed using surfactants that may be included in the example blood cell lysis compositions.

In a first example, a surfactant was targeted to meet the following criteria: the surfactant lyses 100% of blood cells on the timescale of 1 to 2 seconds or less at the concentration tested; the surfactant is compatible with buffers and other chemicals used in the blood cell lysis composition; the surfactant does not interfere with intended optical absorbance measurements; the surfactant does not interact with blood hemoglobin chemistry; the surfactant does not interact with bilirubin chemistry; the surfactant exhibits a relatively low degree of foaming; the surfactant meets established product claims for CO-Oximetry analyzers; and the surfactant is environmentally friendly. The above example criteria are not intended to be limiting in the selection of other surfactants for other blood cell lysis compositions.

Multiple surfactants were screened based on the above criteria. The secondary alcohol ethoxylate Tergitol™ TMN-100X (hereinafter referred to as secondary alcohol ethoxylate1) and Tergitol™ Type 15-S-9 (hereinafter referred to as secondary alcohol ethoxylate2) were both determined to meet the above criteria. The composition of each blood cell lysis composition includes the secondary alcohol ethoxylate in a buffer along with a preservative, as described above.

Table 1 below shows surface tension and foam height at five minutes after the blood cell lysis composition is mixed with water for secondary alcohol ethoxylate1, secondary alcohol ethoxylate2, and Triton-X100 during lysing. Triton-X100 is a control (or reference) surfactant against which the secondary alcohol ethoxylate surfactants are compared. As shown, the foam height for both secondary alcohol ethoxylate1 and secondary alcohol ethoxylate2 is reduced much faster over time than the foam height of surfactant Triton X-100. Similar foam height and fast foam dissipation may be an advantage of secondary alcohol ethoxylates because foaming can cause optical scattering that may interfere with or adversely affect CO-Oximetry measurements. In Table 1 below, "weight % actives" refers to surface tension, which is is a property of the surfactant that indicates/relates to the effectiveness of the material as a surfactant.

TABLE 1

|  | SECONDARY ALCOHOL ETHOXYLATE1 | SECONDARY ALCOHOL ETHOXYLATE2 | TRITON-X100 |
|---|---|---|---|
| Foam height—Initial (0.1 weight % actives) | 150 mm | 124 mm | 128 mm |
| Foam Height—5 minutes (0.1 weight % actives) | 24 mm | 43 mm | 107 mm |
| Surface Tension (1% actives, 25° C.) | 27 dynes/cm | 30 dynes/cm | 33 dynes/cm |

Table 2 below show components of an example blood cell lysis composition. In an example testing procedure, secondary alcohol ethoxylate1 and secondary alcohol ethoxylate2 were included in the example blood cell lysis composition described with respect to Table 2 below at concentrations of 9% to 14% and tested in a CO-Oximetry system of the type described herein.

TABLE 2

| Chemical | Weight % |
|---|---|
| MOPS (3-morpholinopropane-1-sulfonic acid) | 3-5% |

TABLE 2-continued

| Chemical | Weight % |
|---|---|
| NaOH, 2N | 4-8% |
| ProClin ™ 300 | 1-2% |
| secondary alcohol ethoxylate1 or secondary alcohol ethoxylate2 | 9-14% |
| Deionized Water | 71-83% |

The blood cell lysis compositions of Table 2, including secondary alcohol ethoxylate1 or secondary alcohol ethoxylate2, meet the above-described criteria. For example, whole blood samples mixed with blood cell lysis compositions including secondary alcohol ethoxylate1 or secondary alcohol ethoxylate2 exhibited about 100% lysis (for example 90% lysis or greater) of whole blood cells after 1 to 2 seconds. Further, the absorption spectra of calibrating solutions and lysed blood samples obtained at multiple wavelengths were not substantially affected by either test surfactant.

Figure 2:
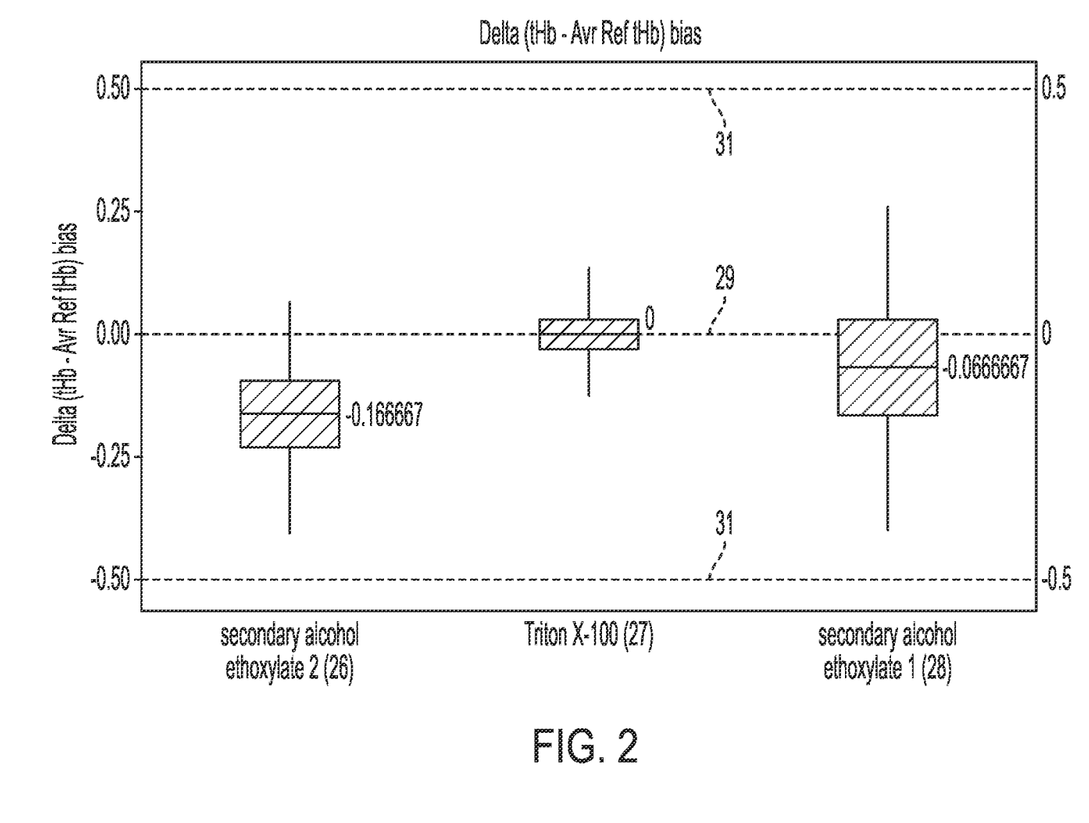
FIG. 2 is a bar graph comparing total hemoglobin (tHb) measurements of two example secondary alcohol ethoxylate blood cell lysis compositions to a control blood cell lysis composition.

FIG. 2 is a bar graph comparing total hemoglobin (tHb) concentration of blood samples mixed with blood cell lysis compositions including secondary alcohol ethoxylate1 28 or blood cell lysis compositions including secondary alcohol ethoxylate2 26 to blood samples mixed with a control blood cell lysis composition including Triton X-100 27. The y-axis represents "Delta (tHb−Avr Ref tHb) bias", which refers to the difference between total hemoglobin concentrations obtained using each of the test blood cell lysis compositions (26 and 28) and the average of the total hemoglobin concentrations, as indicated by the dotted line 29 obtained using Triton X-100 27. The dotted lines 30 and 31 show the analytical range (+0.5 to −0.5) for acceptable bias around average 29 for the blood cell lysis compositions that is based on Triton X-100 27. The blood cell lysis compositions including secondary alcohol ethoxylate1 26 or secondary alcohol ethoxylate2 28 demonstrated total tHb concentration ranges of 7 to 21 g/dL, which is similar to that of the blood cell lysis composition including Triton X-100 27, with only small negative biases. The example data demonstrate that both secondary alcohol ethoxylate1 and secondary alcohol ethoxylate2 may perform as well or better than Triton X-100 27 in blood cell lysis compositions considering speed and completeness of lysis, relatively little or no effect on sample spectra, and accuracy and precision of tHb measurements.

The experiments described below were performed in triplicate. Some experiments were performed on different days as indicated ("12-20" or "01-08").

Figure 3:
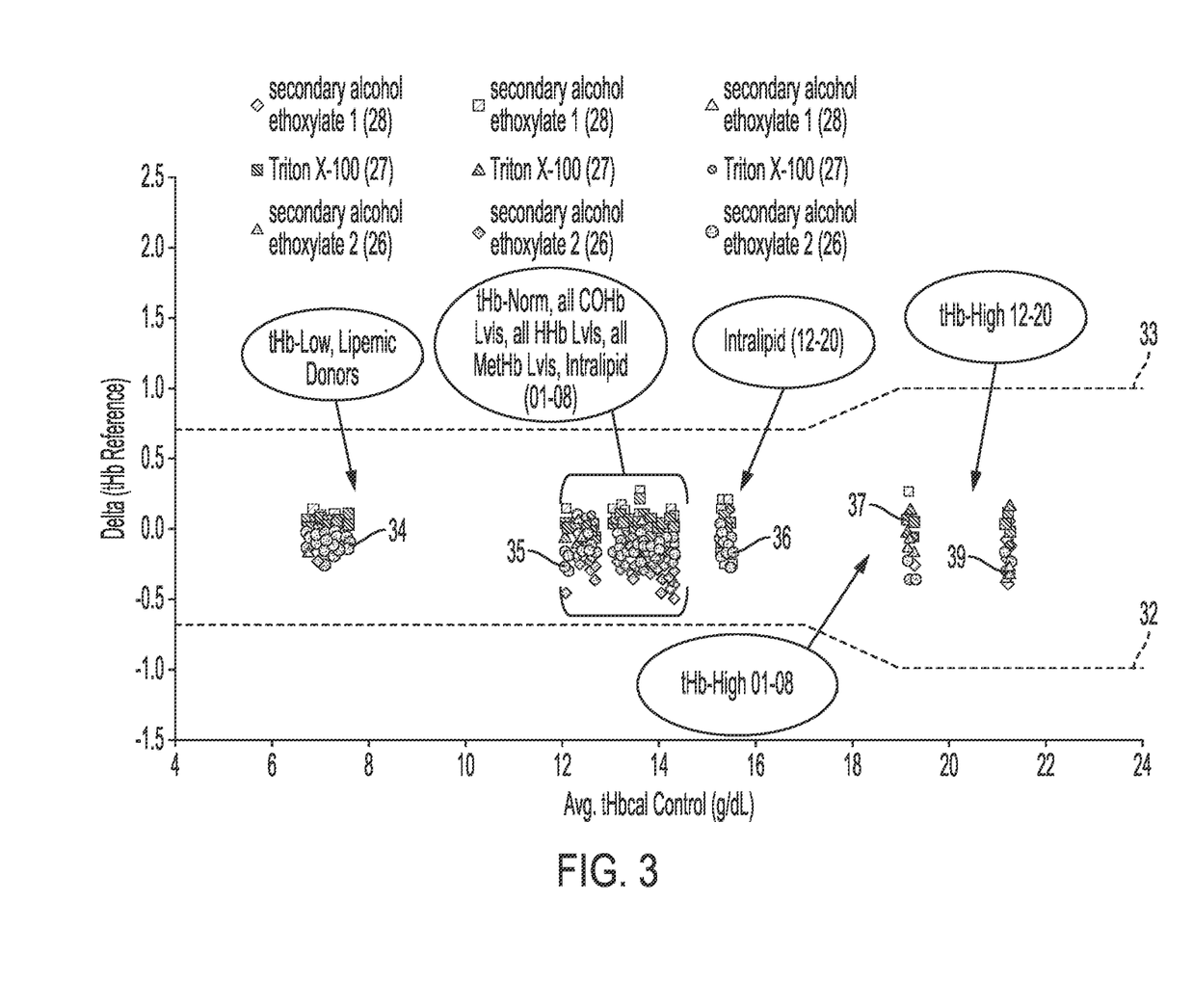
FIG. 3 is a dot-plot showing total hemoglobin (tHb) measurements for two example secondary alcohol ethoxylate blood cell lysis compositions relative to a control blood cell lysis composition.

FIG. 3 is a dot-plot comparing the total hemoglobin (tHb) concentration of blood samples mixed with test blood cell lysis compositions including secondary alcohol ethoxylate1 28 or secondary alcohol ethoxylate2 26 to blood samples mixed with a control blood cell lysis composition including Triton X-100 27. The y-axis represents "Delta (tHb−Reference)," which refers to a difference between total hemoglobin value obtained using the test blood cell lysis compositions to that of the control blood cell lysis composition that includes Triton X-100 27. The x-axis represents "Avg. tHbcal Control (g/dL)" which refers to an average total hemoglobin value in g/dL obtained using the control blood cell lysis composition 27. Values of total hemoglobin obtained using the test blood cell lysis compositions including secondary alcohol ethoxylate1 28, secondary alcohol ethoxylate2 26, and the control blood cell lysis composition that includes Triton X-100 27 are co-plotted. The data demonstrates at least partial overlap at all levels of total hemoglobin.

In this regard, FIG. 3 shows tHb sample measurements from different types of samples, clustered by tHb values (g/dL). Clusters of tHb shown in FIG. 3 include (i) low tHb and lipemic samples 34; (ii) normal tHb, all COHb levels, all HHb levels, and all MetHb levels, and Intralipid™ samples 35; (iii) Intralipid™ samples 36; high tHb samples 37; and high tHb samples 38. Dotted lines 32 and 33 show the analytical range for acceptable bias for the test blood cell lysis compositions. The data demonstrates that both secondary alcohol ethoxylate1 and secondary alcohol ethoxylate2 may perform as well as, or better than, the control blood cell lysis composition that includes Triton X-100 27 when determining total hemoglobin using CO-Oximetry measurements considering speed and completeness of lysis, relatively little or no effect on sample spectra, and accuracy and precision of tHb measurements.

Figure 4:
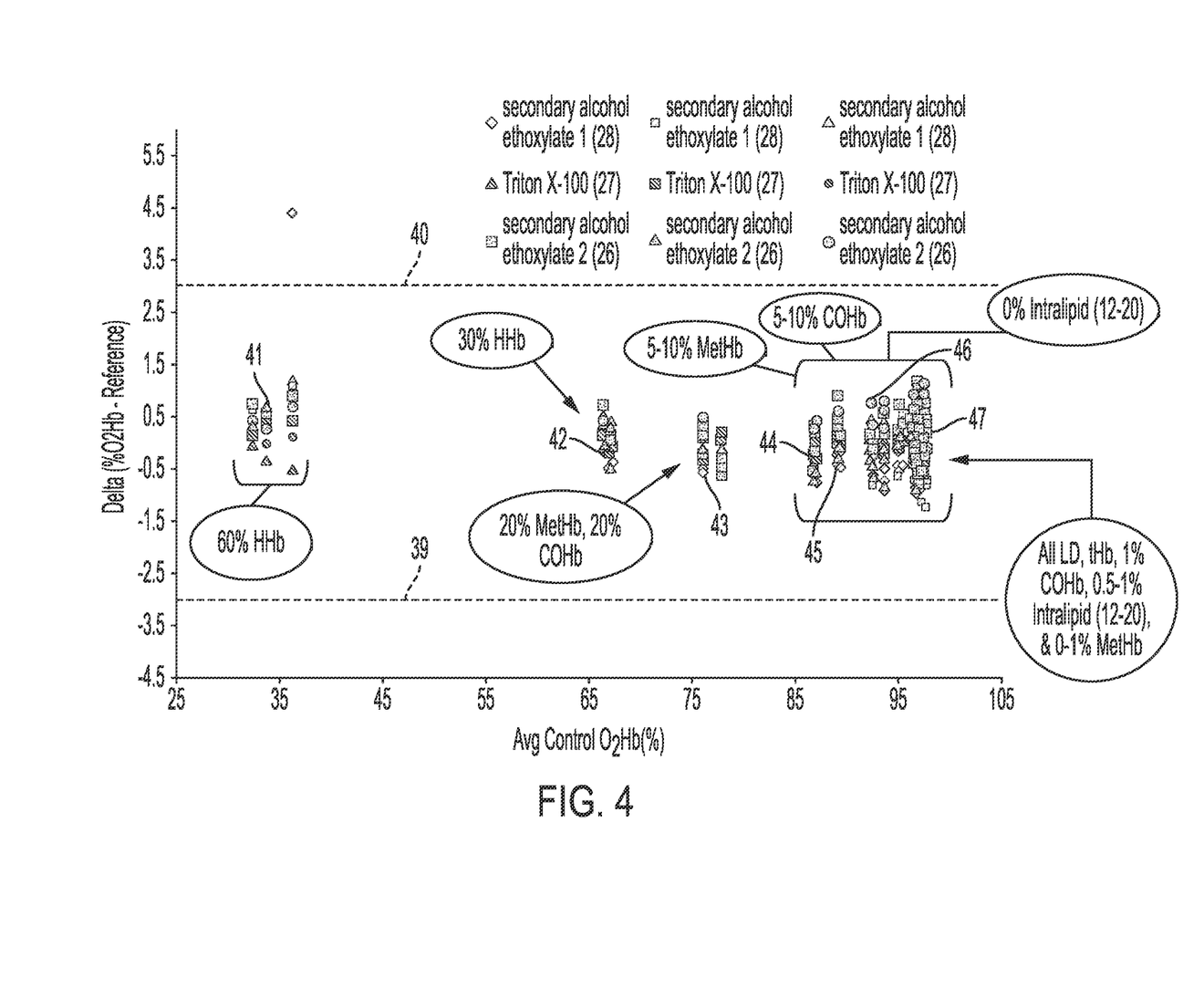
FIG. 4 is a dot-plot showing oxygenated hemoglobin ($O_2Hb$) measurements for two example secondary alcohol ethoxylate blood cell lysis compositions relative to a control blood cell lysis composition.

FIG. 4 is a dot-plot comparing oxygenated hemoglobin ($O_2Hb$) concentration of blood samples mixed with test blood cell lysis compositions of the type described herein that include secondary alcohol ethoxylate1 28 or secondary alcohol ethoxylate2 26 to blood samples mixed with a control blood cell lysis composition including Triton X-100 27. The y-axis represents "Delta (% $O_2Hb$–Reference)", which refers to a difference between oxygenated hemoglobin obtained using each of the test blood cell lysis compositions and that of the control blood cell lysis composition including Triton X-100 27. The x-axis represents "Avg Control $O_2Hb$ (%)", which refers to the percent average of the oxygenated hemoglobin value obtained using the control blood cell lysis composition including Triton X-100 27. Values of oxygenated hemoglobin obtained using blood cell lysis compositions including secondary alcohol ethoxylate1 28, secondary alcohol ethoxylate2 26, and control lysis composition 27 are co-plotted to demonstrate overlap at all levels of oxygenated hemoglobin.

In this regard, the plot of FIG. 4 shows $O_2Hb$ sample measurements from samples clustered by $O_2Hb$ values (g/dL). The clusters of $O_2Hb$ shown include: 60% deoxygenated Hb samples (HHb) 41; 30% HHb samples 42; 20% MetHb and 20% COHb samples 43; 5-10% MetHb samples 44; 5-10% COHb samples 45; 0% Intralipid™ samples 46; and all LD (lipodemic), 1% COHb, 0.5-1% Intralipid™ and 0-1% MetHb samples 47. The dotted lines 39 and 40 show the analytical range for acceptable bias for the test blood cell lysis compositions. The data demonstrate that both secondary alcohol ethoxylate1 and secondary alcohol ethoxylate2 may perform as well as, or better than, the control blood cell lysis composition when determining oxygenated hemoglobin using CO-Oximetry measurements considering speed and completeness of lysis, relatively little or no effect on sample spectra, and accuracy and precision of $O_2Hb$ measurements.

Figure 5:
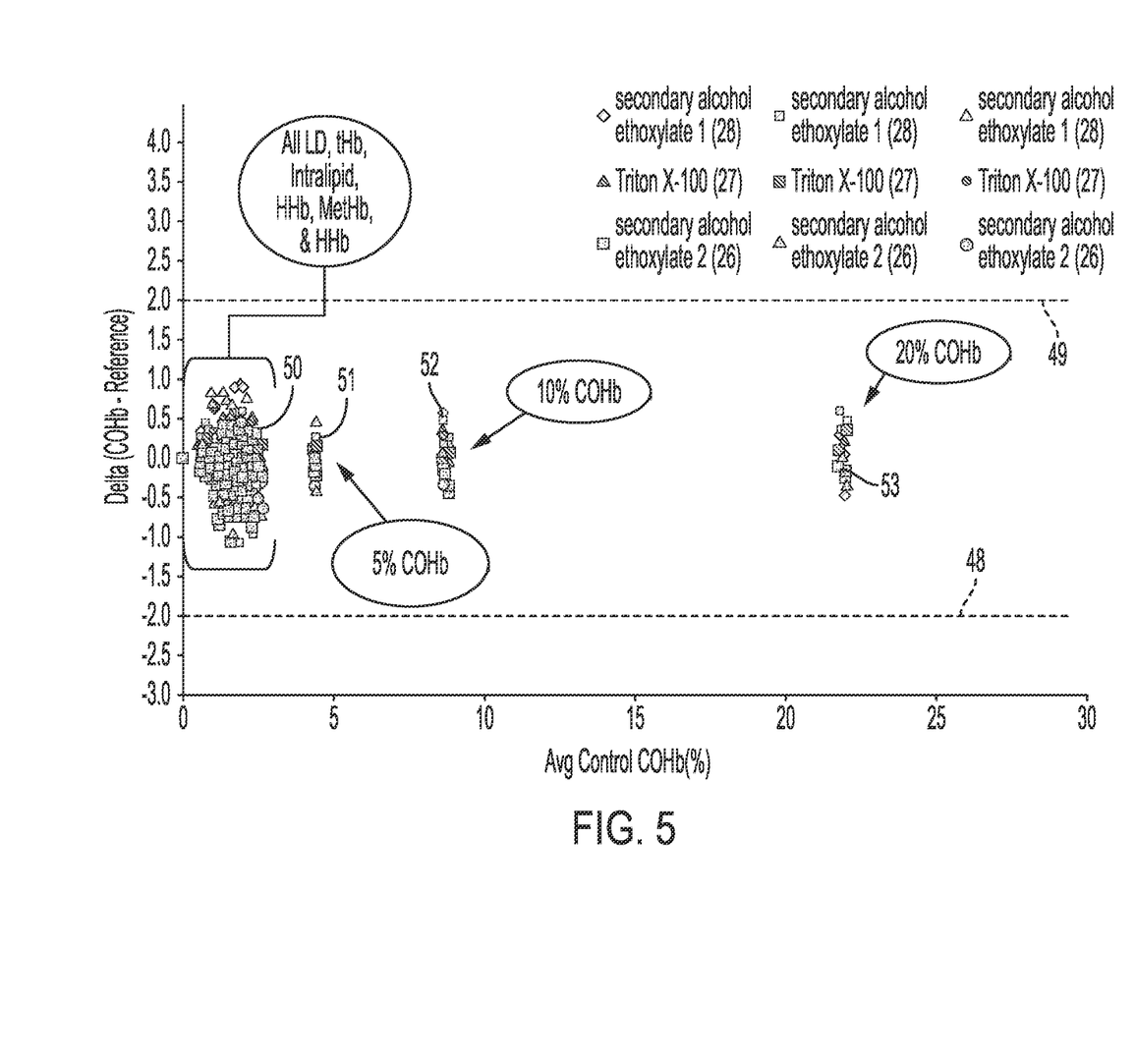
FIG. 5 is a dot-plot showing carboxyhemoglobin (COHb) measurements for two example secondary alcohol ethoxylate blood cell lysis compositions relative to a control blood cell lysis composition.

FIG. 5 is a dot-plot comparing (i) dysfunctional hemoglobin carboxyhemoglobin (COHb) concentration of blood samples mixed with test blood cell lysis compositions including secondary alcohol ethoxylate1 28 or secondary alcohol ethoxylate2 26 to (ii) blood samples mixed with a control blood cell lysis composition including Triton X-100 27. The y-axis represents "Delta (COHb–Reference)", which refers to the difference between carboxyhemoglobin obtained using each of the test blood cell lysis compositions and that obtained using the control cell lysis composition including Triton X-100. The x-axis represents "Avg Control COHb (%)" which refers to the percent average of a carboxyhemoglobin value obtained using blood cell lysis composition 27. Values of carboxyhemoglobin obtained using blood cell lysis compositions including secondary alcohol ethoxylate1 28, secondary alcohol ethoxylate2 26, and the control cell lysis composition 27 are co-plotted and demonstrate overlap at all levels of carboxyhemoglobin.

In this regard, the plot of FIG. 5 shows COHb sample measurements clustered by COHb values (g/dL). Clusters of COHb shown in FIG. 5 include: all LD (lipodemic), tHb, Intralipid™, HHb, and MetHb samples 50; 5% COHb samples 51; 10% COHb samples 52; and 20% COHb samples 53. The dotted lines 48 and 49 show the analytical range for acceptable bias for the test blood cell lysis compositions. The data demonstrates that both secondary alcohol ethoxylate1 and secondary alcohol ethoxylate2 may perform as well or better than the control cell lysis composition including Triton X-100 27 for determining carboxyhemoglobin in CO-Oximetry measurements considering speed and completeness of lysis, no effect on sample spectra, and accuracy and precision of COHb measurements.

Figure 6:
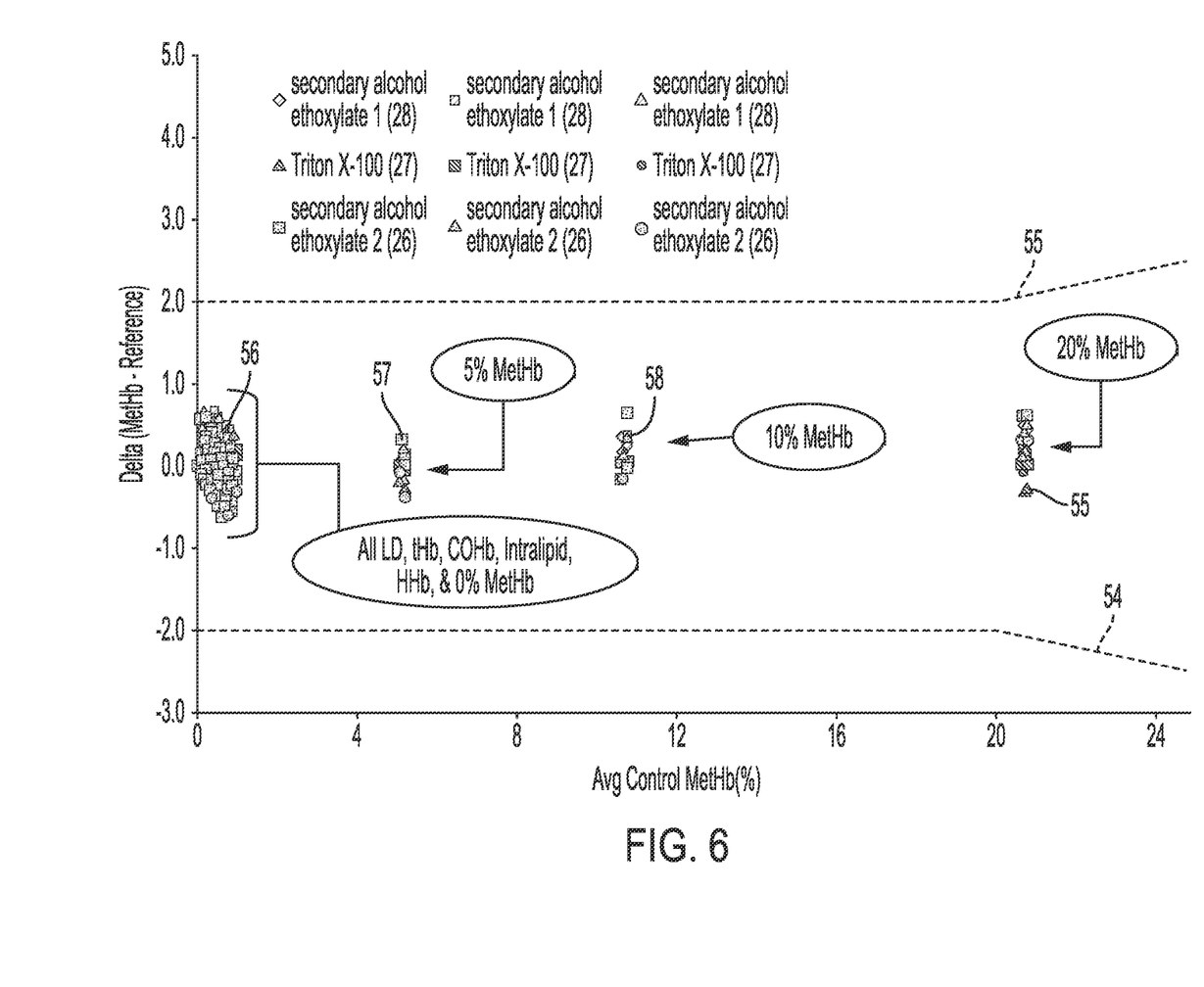
FIG. 6 is a dot-plot showing methemoglobin (MetHb) measurements for two example secondary alcohol ethoxylate blood cell lysis compositions relative to a control blood cell lysis composition.

FIG. 6 is a dot-plot comparing a dysfunctional hemoglobin methemohemoglobin (MetHb) concentration of blood samples mixed with blood cell lysis compositions including secondary alcohol ethoxylate1 28 or secondary alcohol ethoxylate2 26 to blood samples mixed with a control blood cell lysis composition including Triton X-100 27. The y-axis represents "Delta (MetHb–Reference)", which refers to the difference between methemohemoglobin obtained using each of the blood cell lysis compositions to that of the control blood cell lysis composition including Triton X-100. The x-axis represents "Avg Control MetHb (%)", which refers to the percent average of the methemohemoglobin value obtained using the control blood cell lysis composition 27. Values of methemohemoglobin obtained using blood cell lysis compositions including secondary alcohol ethoxylate1 28, secondary alcohol ethoxylate2 26, and the control blood cell lysis composition 27 are co-plotted and demonstrate overlap at all levels of methemohemoglobin.

FIG. 6 shows measurements from donors clustered by MetHb values (g/dL). Clusters of MetHb shown in FIG. 6 include: all LD (lipemic donor), tHb, COHb, Intralipid™, HHb, and 0% MetHb samples 56; 5% MetHb samples 57; 10% MetHb samples 58; and 20% MetHb samples 59. The dotted lines 54 and 55 show the analytical range for acceptable bias for the test blood cell lysis compositions. The data demonstrates that both secondary alcohol ethoxylate1 and secondary alcohol ethoxylate2 may perform as well as. or better than, the reference in blood cell lysis compositions for determining methemohemoglobin in CO-Oximetry measurements considering speed and completeness of lysis, relatively little or no effect on sample spectra, and accuracy and precision of MetHb measurements.

Figure 7:
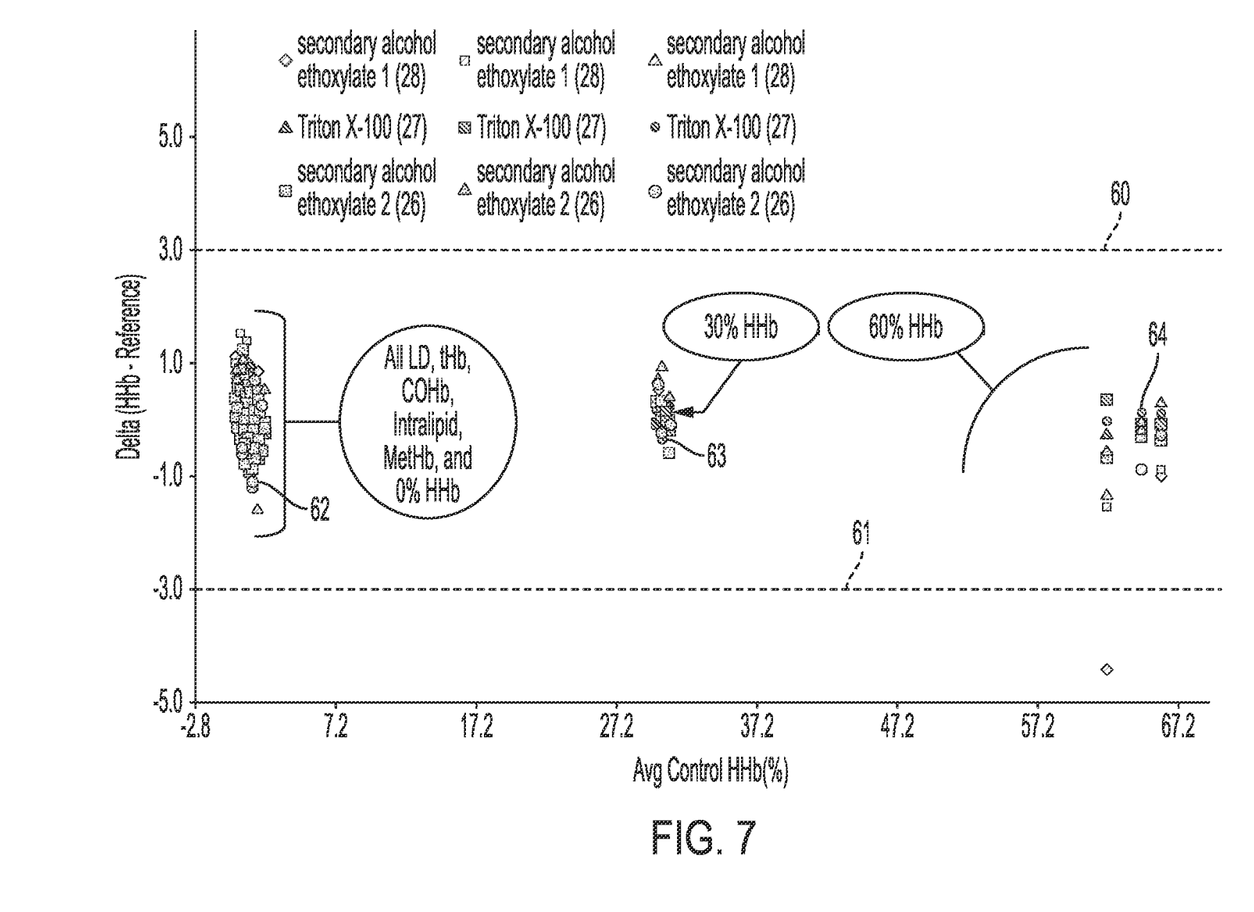
FIG. 7 is a dot-plot showing deoxyhemoglobin (HHb) measurements for two example secondary alcohol ethoxylate blood cell lysis compositions relative to a control blood cell lysis composition.

FIG. 7 is a dot-plot comparing the concentration of deoxyhemoglobin (HHb) concentration in blood samples mixed with blood cell lysis compositions including secondary alcohol ethoxylate1 28 or secondary alcohol ethoxylate2 26 to blood samples mixed with a control blood cell lysis composition including Triton X-100 27. The y-axis represents "Delta (HHb–Reference)", which refers to the difference between deoxyhemoglobin obtained using each of the blood cell lysis compositions to that of the control blood cell lysis composition including Triton X-100. The x-axis represents "Avg Control HHb (%)", which refers to the percent average of deoxyhemoglobin values obtained using the control blood cell lysis composition 27. Values of deoxyhemoglobin obtained using the test blood cell lysis compositions, including secondary alcohol ethoxylate1 28, secondary alcohol ethoxylate2 26, and the control blood cell lysis composition including Triton X-100 2727 are co-plotted. The plot of these values demonstrates overlap at all levels of deoxyhemoglobin.

In this regard, FIG. 7 shows HHb measurements of samples clustered by HHb values (g/dL). Clusters of HHb shown in FIG. 7 include: all LD (lipemic donor), tHb, COHb, Intralipid™, MetHb, and 0% HHb samples 62; 30% HHb samples 63; and 60% HHb samples 64. Dotted lines 60 and 61 show the analytical range for acceptable bias for blood cell lysis compositions containing secondary alcohol ethoxylate1 and secondary alcohol ethoxylate2. The data shows that both secondary alcohol ethoxylate1 and secondary alcohol ethoxylate2 may perform as well as, or better than, the reference in blood cell lysis composition for determining deoxyhemoglobin based on CO-Oximetry measurements considering speed and completeness of lysis, relatively little or no effect on sample spectra, and accuracy and precision of HHb measurements.

The blood cell lysis compositions thus produce tHb, $O_2$Hb, COHb, MetHb, and HHb results within acceptable predefined reference ranges.

In another example, Multi-4 ("M4") is a 3-level control material used in an assay for obtaining human CO-Oximetry blood cell lysis measurements. Table 3 below shows that, for each example 3 level Multi-4 assay performed (L1, L2, and L3), both secondary alcohol ethoxylate1 ("1" in the table) and secondary alcohol ethoxylate2 ("2" in the table) the example blood cell lysis compositions produce tHb, $O_2$Hb, COHb, MetHb, and HHb results within assigned reference ranges ("Range") that are comparable to values produced using control ("Ctrl") blood cell lysis composition that includes Triton-X 100. The acceptable range of result is shown, with "min" referring to the minimum acceptable result and "max" referring to the maximum acceptable result of M4 for each species L1 to L3. Also shown are the average ("ave"), standard deviation ("SD"), and the delta average ("delta") of each secondary alcohol ethoxylate relative to the control average. The data demonstrate that both secondary alcohol ethoxylate1 and secondary alcohol ethoxylate2 may perform as well as, or better than, the control blood cell lysis composition when determining oxygenated hemoglobin using CO-Oximetry measurements considering speed and completeness of lysis, relatively little or no effect on sample spectra, and accuracy and precision of tHb, $O_2$Hb, COHb, MetHb, and HHb measurements

TABLE 3

| | | Range | | Ctrl | | 1 | | | 2 | | |
|---|---|---|---|---|---|---|---|---|---|---|---|
| | Sample | Min | Max | Ave | Std | Ave | Std | Delta | Ave | Std | Delta |
| M4-L1 | tHb | 16.5 | 18.5 | 16.9 | 0.1 | 16.7 | 0.1 | −0.2 | 16.7 | 0.1 | −0.1 |
| | % 02Hb | 40.8 | 45.8 | 41.5 | 0.2 | 41.6 | 0.2 | 0.0 | 41.8 | 0.2 | 0.3 |
| | % COHb | 52.8 | 58.8 | 58.0 | 0.4 | 57.6 | 0.4 | −0.4 | 57.4 | 0.3 | −0.5 |
| | % MetHb | −2.9 | 3.1 | 0.0 | 0.2 | 0.0 | 0.2 | −0.1 | 0.0 | 0.2 | −0.1 |
| | % HHb | — | | 0.5 | 0.4 | 0.9 | 0.3 | −0.4 | 0.8 | 0.2 | 0.3 |
| M4-L2 | tHb | 13.7 | 15.1 | 13.8 | 0.1 | 13.7 | 0.1 | −0.2 | 13.6 | 0.1 | −0.2 |
| | % 02Hb | 92.8 | 97.8 | 97.6 | 0.3 | 96.4 | 0.6 | −0.3 | 96.9 | 0.4 | 0.2 |
| | % COHb | 1.3 | 5.3 | 2.7 | 0.2 | 2.6 | 0.3 | −0.2 | 2.5 | 0.1 | −0.2 |
| | % MetHb | −3.1 | 2.9 | 0.4 | 0.2 | 0.6 | 0.3 | 0.1 | 0.5 | 0.2 | 0.1 |
| | % HHb | — | | 0.1 | 0.3 | 0.5 | 0.6 | 0.4 | 0.1 | 0.4 | 0.0 |
| M4-L3 | tHb | 7.0 | 8.0 | 7.2 | 0.1 | 7.1 | 0.1 | −0.1 | 7.1 | 0.1 | −0.1 |
| | % 02Hb | 74.9 | 79.9 | 77.8 | 0.4 | 77.6 | 0.6 | −0.1 | 78.0 | 0.4 | 0.2 |
| | % COHb | 19.3 | 24.3 | 21.8 | 0.3 | 21.5 | 0.4 | −0.3 | 21.4 | 0.2 | −0.3 |
| | % MetHb | −2.4 | 3.6 | 0.3 | 0.3 | 0.3 | 0.3 | 0.0 | 0.3 | 0.3 | 0.0 |
| | % HHb | — | | 0.2 | 0.4 | 0.6 | 0.7 | 0.4 | 0.3 | 0.3 | 0.1 |

Referring to Table 4 below, blood cell lysis compositions including secondary alcohol ethoxylate1 or secondary alcohol ethoxylate2 also provided very similar (|Delta|<0.1) results to a control blood cell lysis composition that includes Triton X-100 when used to measure the total hemoglobin (tHb) of highly turbid samples. Such samples include naturally occurring turbid samples. In the table below, "LD" refers to lipemic donor (patient) sample identification (ID) as indicated (1-6), and those samples include up to 1% Intralipid-20™.

Table 4 below shows that secondary alcohol ethoxylate blood cell lysis compositions 1 and 2 both produced tHb values close to, or within a standard deviation of, the tHb values produced by the control blood cell lysis composition including Triton-X 100. The data in Table 4 demonstrates that both secondary alcohol ethoxylate1 and secondary alcohol ethoxylate2 may perform as well as, or better than, Triton X-100 in blood cell lysis compositions when determining total hemoglobin based on high lipid blood sample CO-Oximetry measurements.

TABLE 4

| | tHb | | | | | | | |
|---|---|---|---|---|---|---|---|---|
| | Control | | Secondary alcohol ethoxylate1 | | | Secondary alcohol ethoxylate2 | | |
| Lipemic Sample | Ave | SD | Ave | SD | Delta | Ave | SD | Delta |
| LD-1 | 6.9 | 0.1 | 6.9 | 0.1 | 0.0 | 6.8 | 0.0 | −0.1 |
| LD-2 | 7.2 | 0.1 | 7.1 | 0.1 | 0.0 | 7.1 | 0.1 | −0.1 |
| LD-3 | 7.2 | 0.4 | 7.2 | 0.4 | 0.0 | 7.1 | 0.4 | −0.1 |
| LD-4 | 7.1 | 0.4 | 7.1 | 0.4 | 0.0 | 7.0 | 0.4 | −0.1 |
| LD-5 | 7.2 | 0.1 | 7.1 | 0.1 | −0.1 | 7.0 | 0.1 | −0.1 |
| LD-6 | 7.1 | 0.1 | 7.1 | 0.1 | 0.0 | 7.0 | 0.1 | −0.1 |
| 0.5% Intralipid-20 ™ | 14.2 | 1.1 | 14.2 | 1.1 | −0.1 | 14.1 | 1.2 | −0.1 |
| 1% Intralipid-20 ™ | 14.3 | 1.2 | 14.2 | 1.2 | −0.1 | 14.2 | 1.2 | −0.2 |

The blood cell lysis compositions described herein may have one or more the following advantages. As described above, the blood cell lysis compositions may meet one or more target thresholds for: the efficiency and speed with which the blood cell lysis composition lyses blood cells; the degree of interference the blood cell lysis composition exhibits in intended optical measurements; the degree of interference the blood cell lysis composition exhibits in blood hemoglobin chemistry; the degree of interference the blood cell lysis composition exhibits in bilirubin chemistry; and the degree of foaming that causes scattering in optical measurements.

The blood cell lysis compositions described herein, the surfactants contained therein, or both may be biodegradable.

The blood cell lysis compositions and surfactants contained therein have been described with respect to a CO-Oximetry system. However, the blood cell lysis compositions and surfactants contained therein may be used in any appropriate contents and are not limited to use in the context of CO-Oximetry.

The blood cell lysis compositions described herein may be mixed with blood samples from any appropriate mammal, including but not limited to humans, mice, primates, dogs, or livestock for the purpose of blood cell lysis.

At least part of the CO-Oximetry systems described in this specification and their various modifications may be configured or controlled at least in part by one or more computers such as computing systems 17 using one or more computer programs tangibly embodied in one or more information carriers, such as in one or more non-transitory machine-readable storage media. A computer program can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected by a network.

Actions associated with configuring or controlling the test system described herein can be performed by one or more programmable processors executing one or more computer programs to control or to perform all or some of the operations described herein. All or part of the test systems and processes can be configured or controlled by special purpose logic circuitry, such as, an FPGA (field programmable gate array) and/or an ASIC (application-specific integrated circuit) or embedded microprocessor(s) localized to the instrument hardware.

Processors suitable for the execution of a computer program include, by way of example, both general and special purpose microprocessors, and any one or more processors of any kind of digital computer. Generally, a processor will receive instructions and data from a read-only storage area or a random-access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, such as magnetic, magneto-optical disks, or optical disks. Non-transitory machine-readable storage media suitable for embodying computer program instructions and data include all forms of non-volatile storage area, including by way of example, semiconductor storage area devices, such as EPROM (erasable programmable read-only memory), EEPROM (electrically erasable programmable read-only memory), and flash storage area devices; magnetic disks, such as internal hard disks or removable disks; magneto-optical disks; and CD-ROM (compact disc read-only memory) and DVD-ROM (digital versatile disc read-only memory).

Elements of different implementations described may be combined to form other implementations not specifically set forth previously. Elements may be left out of the systems described previously without adversely affecting their operation or the operation of the system in general. Furthermore, various separate elements may be combined into one or more individual elements to perform the functions described in this specification.

Other implementations not specifically described in this specification are also within the scope of the following claims.

What is claimed is:

1. A blood cell lysis composition comprising:
   a buffer; and
   a secondary alcohol ethoxylate at a concentration between 9% weight per volume (w/v) and 20% w/V;
   wherein the secondary alcohol ethoxylate comprises one or more of:
   a first secondary alcohol ethoxylate having the following structural formula where x is 5, 7, 9, 11, 12, 13, 14, or 15, ; or a second secondary alcohol ethoxylate having the following structural formula where n is 6, 10, 11, 12, 13, 14, or 15,

2. The blood cell lysis composition of claim 1, wherein the secondary alcohol ethoxylate comprises:
(a) the first secondary alcohol ethoxylate having the following structural formula where x=9

; or (b) the second secondary alcohol ethoxylate comprising a 70:30 ratio of a third secondary alcohol ethoxylate to a fourth secondary alcohol ethoxylate;
wherein the third secondary alcohol ethoxylate has the following structural formula where n=10 and wherein the fourth secondary alcohol ethoxylate has the following structural formula where n=6:

3. The blood cell lysis composition of claim 1, wherein the buffer comprises at least one of 3-(N-Morpholino) propanesulfonic acid (MOPS), phosphate buffer (PBS), 4-(2-hydroxyethyl)-1-piperazineethanesulfonic acid (HEPES), 2-[1,3-dihydroxy-2-(hydroxymethyl) propan-2-yl]amino]ethanesulfonic acid (TES), 2,2-Bis(hydroxymethyl)-2,2',2''-nitrilotriethanol, or 2-Bis(2-hydroxyethyl)amino-2-(hydroxymethyl)-1,3-propanediol (Bis-Tris).

4. The blood cell lysis composition of claim 1, further comprising a biocide, wherein the biocide comprises at least one of 5-chloro-2-methyl-4-isothiazolin-3-one (CMIT), 2-methyl-4-isothiazolin-3-one (MIT), Proclin 300, 1,2-Benzisothiazolin-3-one (BIT), dodecylguanidine hydrochloride (DGH), gentamycin, levofloxacin, colistin, octylisothiazolinone (OIT), or amikacin.

5. The blood cell lysis composition of claim 4, wherein the biocide comprises CMIT and MIT.

6. The blood cell lysis composition of claim 5, wherein the CMIT and the MIT are in a ratio of about 3:1 (CMIT: MIT).

7. The blood cell lysis composition of claim 6, wherein the CMIT: MIT is at a concentration of 1% w/v in the blood cell lysis composition.

8. The blood cell lysis composition of claim 1, wherein the blood cell lysis composition has a pH between about 6 and about 8.

9. The blood cell lysis composition of claim 1, wherein the secondary alcohol ethoxylate is present at a concentration between 9% to 11% w/v, between 9 to 10% w/v, between 9.0% to 9.5% w/v, between 10% to 12% w/v, between 10% to 11% w/v, between 10.0% to 10.5% w/v, between 11% to 13% w/v, between 11% to 12% w/v, between 11.0% to 11.5% w/v, between 12% to 14% w/v, between 12% to 13% w/v, between 12.0% to 12.5% w/v, between 13% to 14% w/v, or between 13.0% to 13.5% w/v.

10. The blood cell lysis composition of claim 1, wherein the secondary alcohol ethoxylate is present at a concentration in a range of about 9% to about 14% w/v.

11. The blood cell lysis composition of claim 1, wherein the secondary alcohol ethoxylate is biodegradable.

12. The blood cell lysis composition of claim 1, wherein the composition is configured to lyse at least 90% of blood cells in a sample in less than 2 seconds.

13. The blood cell lysis composition of claim 1, wherein the secondary alcohol ethoxylate has a 5 minute foam height from about 75 millimeter (mm) to about 125 mm.

14. The blood cell lysis composition of claim 1, wherein the secondary alcohol ethoxylate has a 5 minute foam height from about 40 mm to about 75 mm.

15. A method for determining a level of a hemoglobin in a blood sample, the method comprising:
(i) mixing the blood cell lysis composition of claim 1 with the blood sample, thereby lysing one or more cells in the blood sample; and
(ii) determining the level of the hemoglobin in the blood sample.

16. The method of claim 15, wherein the hemoglobin comprises at least one of oxyhemoglobin, de-oxyhemoglobin, carboxyhemoglobin, methemoglobin, sulfhemoglobin, cyanmethemoglobin, or fetal hemoglobin.

17. The method of claim 15, further comprising measuring a level of bilirubin in the blood sample.

* * * * *